United States Patent
Felici et al.

(10) Patent No.: US 12,201,853 B2
(45) Date of Patent: Jan. 21, 2025

(54) DEVICE FOR THE RADIOTHERAPY TREATMENT OF CANCER PATIENTS

(71) Applicant: S.I.T.—Sordina IORT Technologies S.p.A., Vicenza (IT)

(72) Inventors: Giuseppe Felici, Vicenza (IT); Giuseppe Carella, Vicenza (IT); Massimo Di Francesco, Vicenza (IT); Salvatore Barone, Vicenza (IT); Luigi Faillace, Vicenza (IT); Mauro Migliorati, Vicenza (IT); Bruno Spataro, Vicenza (IT); Luigi Palumbo, Vicenza (IT); Andrea Mostacci, Vicenza (IT)

(73) Assignee: S.I.T.—Sordina IORT Technologies S.p.A., Vicenza (IT)

( * ) Notice: Subject to any disclaimer, the term of this patent is extended or adjusted under 35 U.S.C. 154(b) by 411 days.

(21) Appl. No.: 17/762,096

(22) PCT Filed: Aug. 10, 2020

(86) PCT No.: PCT/IT2020/050203
§ 371 (c)(1),
(2) Date: Mar. 21, 2022

(87) PCT Pub. No.: WO2021/053699
PCT Pub. Date: Mar. 25, 2021

(65) Prior Publication Data
US 2022/0323792 A1 Oct. 13, 2022

(30) Foreign Application Priority Data
Sep. 19, 2019 (IT) .................. 102019000016760

(51) Int. Cl.
*A61N 5/10* (2006.01)
*A61B 6/42* (2024.01)

(52) U.S. Cl.
CPC .............. *A61N 5/1049* (2013.01); *A61B 6/42* (2013.01)

(58) Field of Classification Search
CPC ............................... A61N 5/1049; A61B 6/42
See application file for complete search history.

(56) References Cited

U.S. PATENT DOCUMENTS

| | | | |
|---|---|---|---|
| 6,268,727 B1 * | 7/2001 | King | G01F 1/716 324/306 |
| 2017/0303384 A1 | 10/2017 | Aoki et al. | |
| 2019/0187198 A1 * | 6/2019 | Anderson | G01R 29/0878 |

FOREIGN PATENT DOCUMENTS

| | | |
|---|---|---|
| EP | 0700578 | 3/1996 |
| EP | 1782858 | 5/2007 |
| WO | WO 94/14304 | 6/1994 |

(Continued)

OTHER PUBLICATIONS

International Search Report and the Written Opinion Dated Nov. 25, 2020 From the International Searching Authority Re. Application No. PCT/IT2020/050203. (10 Pages).

*Primary Examiner* — Nicole M Ippolito (57) ABSTRACT

Described is a device for radiotherapy treatment with a high dose rate of ionizing radiation, comprising an accelerating guide (11) of a medical radiofrequency accelerator, at least two simultaneously thermostated resonant cavities (10) and comprising a first pick-up (12), a second pick-up (12B) in at least two resonant cavities (10) and an optical system (20) of the beam.

6 Claims, 4 Drawing Sheets

(56) References Cited

FOREIGN PATENT DOCUMENTS

| WO | WO 94/23439 | 10/1994 |
| WO | WO 2012/149044 | 11/2012 |
| WO | WO 2014/195986 | 12/2014 |

\* cited by examiner

DEVICE FOR THE RADIOTHERAPY TREATMENT OF CANCER PATIENTS

RELATED APPLICATIONS

This application is a National Phase of PCT Patent Application No. PCT/IT2020/050203 having International filing date of Aug. 10, 2020, which claims the benefit of priority Italian Patent Application No. 102019000016760 filed on Sep. 19, 2019. The contents of the above applications are all incorporated by reference as if fully set forth herein in their entirety.

FIELD AND BACKGROUND OF THE INVENTION

This invention relates to a device for the radiotherapy treatment of cancer patients.

In particular, the invention relates to a device which, besides being suitable for the instantaneous measurement of the dose emitted by pulse during a radiotherapy treatment, is able to measure the energy of a beam of ionizing radiation; moreover, the beam of ionizing radiation has a much higher energy rate than the prior art.

The invention also relates to a radiotherapy machine, for example, intraoperative (IORT), equipped with such a device.

This is achieved by means of a charged particle accelerator for high current radiotherapy, which, through a real-time non-destructive control of the dose deposited at a point and through a control of the energy of the radiotherapy beam, as well as through a comparison between them, allows the prospect of a positive prognosis given by a radiotherapy treatment to be optimized.

It is well known that radiotherapy is an established tool in the treatment of cancer patients and together with surgery and chemotherapy has significantly improved both the final prognosis and the quality of life of patients.

Radiotherapy consists of irradiation of the tumour mass, tumour residue and/or surgically exposed tumour bed through a collimated electron beam.

Among the most feared diseases of our time, there is no doubt that cancer is to be considered as a major disease because of the high mortality rate which some types have and because of the difficulties of treatment.

The tumour, also called neoplasia or cancer, if malignant, is a class of diseases characterized by uncontrolled reproduction of certain cells of the body, which stop responding to physiological mechanisms of cellular control as a result of damage to the genetic assets.

A cell, in order to become tumorous, must "go mad", that is, there must be an error in the system which controls its reproduction.

In fact, all cancerous and precancerous cells have very extensive alterations in their chromosome structure; in particular, the number of chromosomes present in their nucleus is altered and the chromosomes themselves may be damaged, multiple or be missing.

This random genetic disorder explains the extreme variability in appearance, effects, symptoms and prognosis of the many known forms of cancer.

Although the general mechanism of origin of tumours is unique, they can manifest a very wide range of evolutions and symptoms.

In all cases of cancer there is a constant increase in the number of cancer cells due to their greater speed of cellular reproduction.

Thus, more cancer cells multiply and fewer of them die, whilst those that survive continue to multiply.

The critical size of a tumour is about one cubic centimetre; once this size is reached, the tumour starts to grow very quickly giving rise to the first symptoms, which are often ignored or underestimated, and become detectable through medical examinations and analyses.

The large speed of reproduction of cancer cells is at the root of the need and urgency for treatment as quickly and as drastically as possible, that is to say, in order to eliminate all neoplastic cells with the greatest possible degree of certainty, in order to avoid the possibility of possible recurrences.

Through surgery, if possible, an attempt is made to remove what is called a tumour mass, that is, the set of mutated cells and what surrounds them.

This method of treatment cannot always be used or, when used, is not always sufficient to ensure the desired result.

It is not possible to know whether the tumour has also affected the surrounding or adjacent cells, which appear to be healthy; moreover, it is possible that the surgical operation itself leads to a dissemination of tumour cells.

For these reasons, chemotherapy and radiotherapy are also used in combination or as an alternative to surgery.

Chemotherapy exploits the specific sensitivity of individual tumours to certain chemical substances.

A personalized mixture of several drugs is studied for each patient and almost always, in this mixture, one or more inhibitors of the mitosis are present to obstruct cell proliferation.

However, these are responsible for some serious and undesirable side effects, such as hair and skin loss, which afflicts patients undergoing chemotherapy.

Radiotherapy is an established tool in the treatment of cancer patients and consists of irradiation, through ionizing radiation, of neoplastic tissue and/or tissue adjacent to neoplasia.

The effectiveness associated with radiotherapy treatment lies in the possibility of striking diseased cells with a sufficiently high dose to be curative while healthy cells are spared, that is, they are irradiated with a sub-lethal dose, which allows them to heal.

Figure 1:
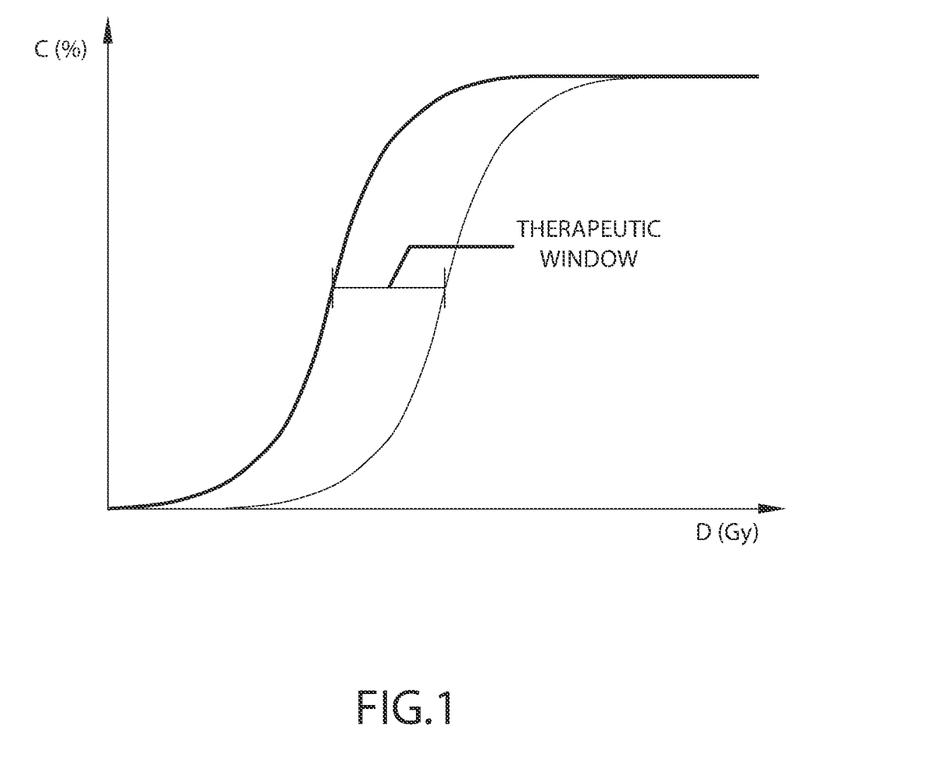
FIG. 1 schematically shows a diagram relative to the known concept of "therapeutic window" in radiotherapy.

In a further analysis, the effectiveness of a radiotherapy treatment is given by the possibility of having a "therapeutic window" (see the attached diagram in FIG. 1, in which the "therapeutic window" is defined as the distance between the curves) between the curative dose to the target (upper curve in FIG. 1) and the damage to healthy tissue (lower curve in FIG. 1).

The prognosis is closely related to the existence of this "therapeutic window"; the tumours with a more complex prognosis are those where it is complicated and sometimes impossible to limit the doses to tissues close to the target, below the limit of complications.

As a result, radiotherapy also has undesirable effects.

In fact, like chemotherapy, it considerably weakens the body and subject the patient's healthy organs to its direct effects, even if only partially.

In both cases, therefore, it is important to be able to minimize their application so as not to make the side effects too significant.

The technological development of recent years has led, through the development of different technologies and through the use of increasingly sophisticated "imaging" techniques, to the optimization of the deposition of the ionizing radiation dose on the target, ensuring the protection of the healthy tissue of the critical organs.

Currently, in order to carry out selective radiotherapy treatment, limited, as far as possible, to neoplastic tissues, various strategies are implemented, such as:
(a) optimisation of the ballistics of the radiation beam, whereby different ionizing radiation and technologies are chosen according to the tumour to be treated, using, with external beams, different beam entry fields;
(b) optimisation of radiobiological parameters, with the exception of IORT (intraoperative radiotherapy), which consists of the administration of a high dose of ionizing radiation.

The standard technique in radiotherapy is represented by a treatment split into a series of treatments of 2 Gy per day (Gy=Gray, the unit of measurement of the absorbed radiation dose of the International System), to be repeated until the prescribed dose is reached (60-80 Gy).

Radiotherapy is currently administered through multiple devices: radioisotopes, linear accelerators in electron and/or X-ray mode, cyclotrons for protons and/or carbon ions.

All these technologies have in common, however, a variable dose rate but substantially limited to a few Gy per minute.

Some research has shown that, using a much higher dose rate, defined as the "Flash" effect, the absorbed dose obtained was higher than the standard dose by a factor greater than 1000, equal to approximately 40 Gy/s.

Thanks to this "Flash" effect, the ratio between the damage to diseased cells with respect to the healthy tissue was no longer that achievable with standard dose rates, but much more advantageous.

In this way, the so-called "therapeutic window" (see the diagram in FIG. 1) was significantly larger, suggesting a higher probability of a positive prognosis for tumours which are not yet curable.

The problem at the base of the invention, as it is an unprecedented challenge, is that of being able to make this discovery usable in the clinical field, developing a reliable technology which allows the implementation of the technique in a truly feasible and usable product.

The technical standard EN 60601-2-1, ed. III, regarding the safety performance of a medical accelerator in the 1-50 MeV range requires that the output beam of a particle accelerator (for example, of a LINAC) be controlled in real time, pulse by pulse, so as to ensure the precision of the dose delivered and to avoid dangerous over-dosages, which could lead to deterministic harm such as patient death, or under-dosages, which would render the treatment ineffective.

Therefore, for the reasons explained above, an element common to any particle accelerator intended for radiotherapy is the need to include a system for the real-time measurement of the output ionizing radiation and the ionizing radiation dose to be sent to the target for each emitted radiation pulse.

SUMMARY OF THE INVENTION

The main aim of the invention is, therefore, to make a device for the radiotherapy treatment of cancer patients, which implements the so-called "flash" effect and also allows the precise measurement of the dose delivered by the high beam current.

Moreover, the presence of a very high beam charge implies that this technology not only needs to measure the output dose of a medical accelerator in real time, but requires real-time control of the generated beam energy. In fact, if the charge of the beam energy generated becomes comparable with the power absorbed by the accelerating structure, a current fluctuation also implies an energy variation.

Therefore, for high currents the energy measurement cannot be separated from the current measurement, as will be described in detail below.

A further aim of the invention is to make an accelerator operating in "Flash" mode which must be able to reach up to 1 Gy/p, three orders of magnitude of absorbed dose higher than traditional linear accelerators.

It must then be considered how a "Flash" treatment, for the characteristics described here, is obviously carried out in an extremely short time and with a very small number of pulses compared to the standard.

By way of an example, considering the IORT single dose treatment of breast cancer, 21 Gy prescribed at 90% isodose (approximately 23.3 Gy at 100% isodose) are administered.

With the accelerators currently on the market (maximum dose rate 30 Gy/min, repetition frequency 10 Hz) this treatment is performed in approximately 46.6 s with a number of pulses equal to 466.

The same treatment, performed for example in "Flash" mode at 500 Gy/s, with a repetition frequency equal to 300 Hz, would last less than 0.047 seconds and the entire dose would be delivered in just 14 pulses.

The monitoring of each pulse in "Flash" mode therefore becomes even more crucial than it already was for conventional radiotherapy.

Another aim of the invention is to make a device for the radiotherapy treatment of cancer patients, the minimum characteristics of which are designed to comply with the technical standard EN 60601-2-1, ed. III.

A further aim of the invention is to make a device for the radiotherapy treatment of cancer patients which is of reasonable size and cost, and whose installation is possible in a bunker and/or operating room which is not overly specialized and/or RF shielded.

These and other aims are achieved by a device for the radiotherapy treatment of cancer patients according to the accompanying claim 1; other detailed technical features are contained in the subsequent claims.

A device for the radiotherapy treatment of cancer patients with high energy incorporated in a high-dose radiotherapy machine is also the object of the invention.

The treatment device which is the object of the invention is advantageous compared to traditional devices.

More specifically, the technology commonly used for real-time monitoring of the constancy of the output beam comprises the use of ionization and crossing chambers.

However, this technology has at least two different criticalities when used with the "Flash" methodology described above:
the ionization chambers, at high dose per pulse, lose linearity between charge released for ionization and dose;
the beam incident on the electrodes of the chamber has a sufficiently high current to generate overheating and ablation phenomena, thereby making the use of this technology extremely problematic.

In addition, the proposed device, as will be illustrated below, allows a direct measurement of the current, immediately related to the arrangement of dose on the target.

Working with very high beam currents, if they are comparable with the power absorbed by the accelerating structure, a current fluctuation implies a variation in energy which must be controlled and, consequently, it is necessary to have a further control of the beam energy; a simple mathematical demonstration follows to prove this.

The power generated by the radio frequency source (magnetron or klystron) is distributed according to the equation, where WRF is the power of the radio frequency source, WBEAM is the power absorbed by the beam and WLOSS is the power lost:

$$W_{RF} = W_{LINAC} + W_{BEAM} + W_{LOSS}$$

The final mean kinetic energy of the beam can be expressed approximately as $$V_{BEAM} = \sqrt{W_{LINAC} \cdot Z_{LINAC}}$$

where VBEAM is the mean kinetic energy of the accelerated beam and ZLINAC is the resonance impedance of the accelerating structure, while the power absorbed by the beam is given in first approximation by $$W_{BEAM} = V_{BEAM} \cdot I_{BEAM}$$

where IBEAM is the beam current.

By way of an example, a 10 MeV S-band accelerating structure is considered, operating in π/2 mode, which typically has an impedance equal to approximately 90 MΩ, and a 120 mA beam accelerated to 10 MeV. By using the above equations, the power absorbed by LINAC is equal to approximately 1.1 MW while the power absorbed by the beam is equal to 1.2 MW.

Since the two terms are comparable, it is evident that a change in current implies a significant change in energy (unlike conventional radiotherapy), and it is therefore necessary to also monitor this parameter in real time.

BRIEF DESCRIPTION OF THE SEVERAL VIEWS OF THE DRAWINGS

These and other aims are achieved by a device for the radiotherapy treatment of cancer patients, as will be described in detail below, according to a preferred but not exclusive embodiment of the invention and with reference to the accompanying drawings, in which:

FIG. 2 schematically shows a lateral and longitudinal cross-section view of a passive resonant cavity operating in vacuum, connected to the accelerating structure of the device for the radiotherapy treatment of cancer patients, according to the invention;

FIG. 3 is a partial and cross-section view of the resonant cavity of the device for radiotherapy treatment of cancer patients, connected to an accelerator charged particle source, according to the invention;

DESCRIPTION OF SPECIFIC EMBODIMENTS OF THE INVENTION

Figure 2A:
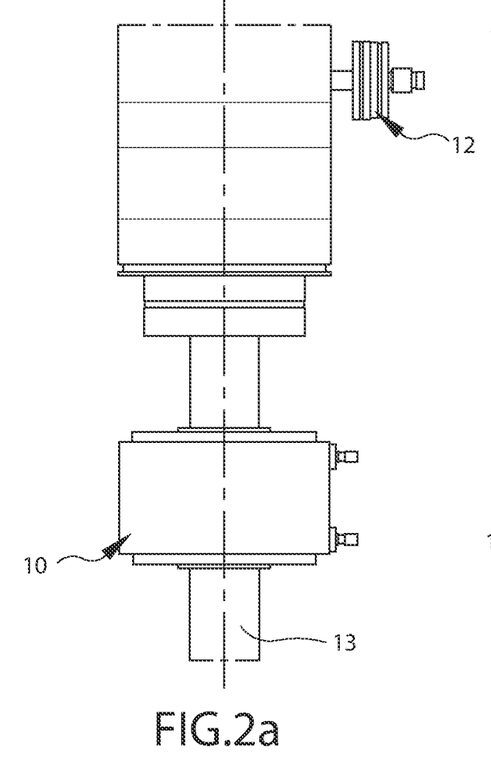
FIG. 2a is a side view of FIG. 2.
Figure 2B:
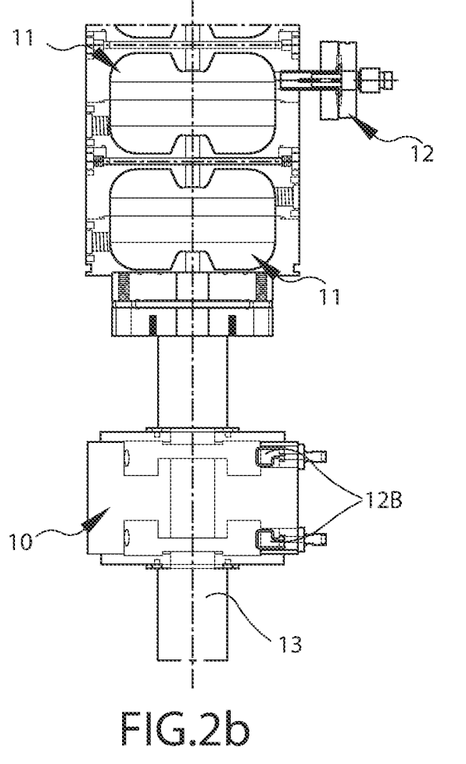
FIG. 2b shows a detail of the longitudinal cross-section view of FIG. 2.
Figure 3A:
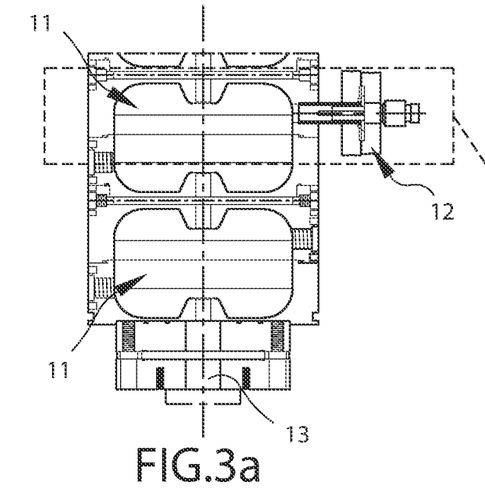
FIG. 3a is a front view of the resonant cavity in FIG. 3.
Figure 3B:
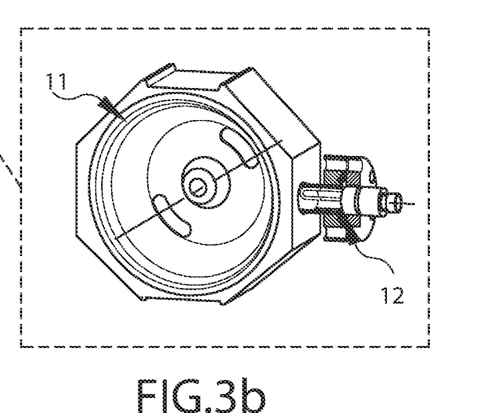
FIG. 3b is an enlarged cross-section view of the resonant cavity and loop of FIG. 3.
Figure 4:
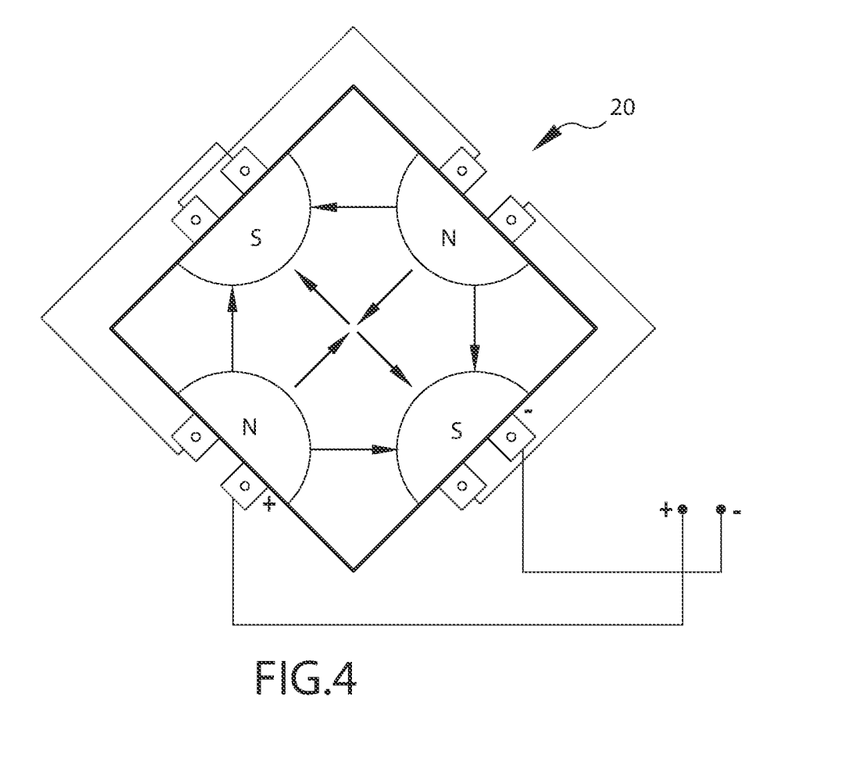
FIG. 4 shows schematically an example of a quadrupole optical beam system according to the invention.
Figure 5:
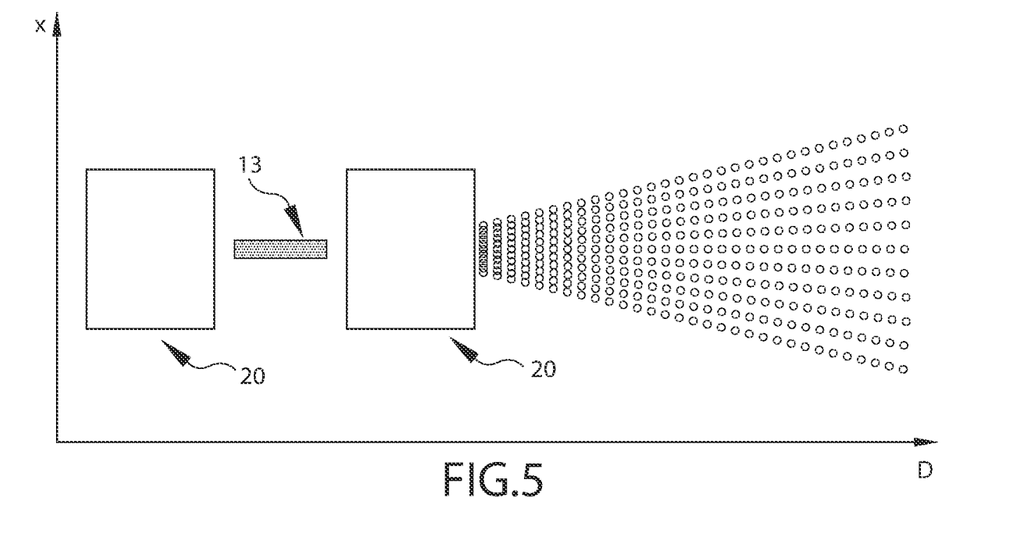
FIG. 5 shows schematically a preliminary simulation of electron beam de-focussing with the quadrupoles of FIG. 4.

With reference to the above-mentioned drawings, the dose monitoring device, which is the subject of the invention, as shown in FIGS. 2 and 3, is placed at the outlet of the medical charged particles accelerator.

In particular, the device includes at least two passive resonant cavities 10 (FIG. 3b) mechanically joined together.

Said passive resonant cavities 10 are positioned after the accelerating guide 11, along the axis of the current beam 13 (FIGS. 2a and 2b) and are oriented in such a way that their surface is perpendicular to the magnetic field lines generated by the passage of the beam current.

Positioned within each of said cavities 10 and in a position distant from the axis of the ionizing radiation beam, there is a pick-up 12B, such as a loop or coil.

The coil 12B is placed orthogonally to the azimuth direction, therefore orthogonal to the magnetic field generated by the beam along the direction 13.

The signal taken from the pick-up 12B is then processed by an electronic beam control board that communicates with a user interface.

The energy of the accelerated particle beam is, on the other hand, measured thanks to the pick-up 12 positioned inside the accelerating guide. The details are discussed below; the signal taken from the pick-up 12 is also sent to the above-mentioned electronic board.

Adjacent and subsequent to the passive cavities 10, with respect to the direction of the particle beam 13, there is an optical system 20 of the beam, for example a quadrupole.

Each of the said passive resonant cavities 10 is tuned to the same resonance frequency in the way said accelerating guide 11 operates.

A passive resonant cavity 10 allows measurement in a non-destructive manner of the current of a charged particle beam and the measurement of the beam current is intrinsically proportional to the absorbed dose.

In fact, the definition of dose gives:

$$D_{pulse} = \frac{dE}{dm}$$

For a single pulse:

$$D_{pulse} = \frac{dE}{dm} = \frac{E_{pulse}}{m(E)^*} = \frac{\int_0^{T_{pulse}} V_{beam}(t) \cdot I_{beam}(t) dt}{m(E)^*}$$

where Vbeam is the mean kinetic energy of the pulse, Ibeam is the current, m(E)* is the mass where the electrons deposit all the transported energy and Tpulse is the temporal duration of the pulse.

Since the treatment is carried out with fixed energy, the above equation shows that the measurement of the beam current makes it possible to immediately evaluate the dose deposited on the target.

It should be noted that this device can advantageously replace the ionization chamber-based measurement system for all the accelerators which use charged particles (electrons, protons, ions, etc.).

The resonant cavities 10 can be simultaneously thermostated and made in such a way as to measure the dose independently of each other according to the requirements of EN 60601-2-1.

The device can obviously be implemented for any radiofrequency accelerator structure, regardless of the working frequency (L, S, C or X band); in particular, the device provides a direct measurement of the dose for all the medical accelerators which use charged particles, whether they are electrons, protons or ions.

The operation of the device for the radiotherapy treatment of cancer patients, implementing the "Flash" effect, according to the invention, is substantially referable to the following phases:
a) real-time non-destructive testing of the dose deposited at a point through the above-mentioned passive cavities 10;
b) beam energy control through the coil or pickup 12;
c) design of the beam optics, for example by means of a quadrupole system 20.

The current accelerated by the LINAC powered by a radiofrequency source (klystron, magnetron) can always be represented as a Fourier series of sines only, with a fundamental frequency equal to the frequency ω0 of the accelerating guide operating mode, in the following way:

$$I(t) = \sum_{n=1}^{\infty} I_n \sin(n\omega_0 t)$$

The magnetic field generated by the electron beam at the coil is given by:

$$|\vec{B}_{TOT}(t)| = \frac{\mu_0}{2\pi d} I(t)$$

whilst the field actually detected, due to the filtering effect of the resonant cavity, is $$|\vec{B}(t)| = \frac{\mu_0}{2\pi d} I_1 \sin(\omega_0 t)$$

where d is the distance between the electron beam and the centre of the coil, μ0 is the magnetic permeability of the vacuum and I1 is the first harmonic.

The passive resonant cavities 10 are tuned so as to have a resonance frequency equal to ω0 at the desired operating temperature and the voltage measured at the ends of the coil is as follows:

$$V(t) = -\frac{\partial}{\partial t}\Phi(B(t)) = -\frac{\partial}{\partial t}\int_A B(t)ds = -\frac{\partial}{\partial t}B(t)A = -\frac{\mu_0}{2\pi d}A\omega_0 I_1 \cos(\omega_0 t),$$

where A is the area of the coil.

The signal, integrated over time by means of a special electronic circuit, thus provides a measurement intrinsically proportional to the charge carried by the beam and, therefore, to the dose deposition.

Each cavity can be made of metallic and non-metallic material.

When the cavities are made of metal material, the material of each resonant cavity 10 is chosen in such a way as to simultaneously meet the need to ensure efficient thermostating of the double resonant cavity; moreover, two resonant cavities 10 are advantageously used to measure the beam current.

The cavities can be advantageously made of non-metallic material, suitable for the vacuum, for example KOVAR or PYREX glass and covered, by deposition, with a thin metal layer, for example, copper and/or aluminium.

In this way the wall thickness of the cavity is calculated in such a way as to absorb any incident electrons before they interact with the metal components inside the cavity (such as, for example, the thin layer of copper deposited on the inner walls and/or the pick-up).

It is sufficient to design the thickness of the upper face which is able to reduce the energy of the incident electrons to less than 0.5 MeV.

This demonstration can be carried out by means of simulations using the Monte Carlo method or, as a first approximation, with the CSDA model.

The thickness of the copper deposition depends on the working frequency of the accelerator and is calculated using the formula which calculates the skin depth δ, defined as follows:

$$\delta = \sqrt{\frac{1}{\pi \sigma \mu_0 f}}$$

where f is the frequency of the electromagnetic wave in cavities, $\mu_0 = 4\pi \cdot 10^{-7}$ is the vacuum permeability and σ is the electrical conductivity of the metal.

By way of example, but not exhaustive, the following details the design of a cavity to measure a beam accelerated by a LINAC operating at 2.998 GHz (S-band) with maximum energy equal to 10 MeV.

With RCSDA (Pyrex) at 10 MeV≈5.69 g/cm2 and Pyrex density≈2.23 g/cm3, the thickness TH of the Pyrex body of the cavity is easily calculated with the formula:

$$E_{out} = E_{in} \cdot \left(1 - \frac{TH}{\frac{R_{CSDA}}{\rho}}\right) \rightarrow TH = \frac{R_{CSDA}}{\rho} \cdot \left(1 - \frac{E_{out}}{E_{in}}\right)$$

This thickness TH is approximately 2.2 cm for an incident beam with energy Ein equal to 10 MeV and an outgoing beam with energy Eout equal to 0.5 MeV.

On the other hand, the thickness of copper to be deposited inside the cavity must be not less than the skin depth at 2.998 GHz, that is, approximately 1.2 μm, calculated according to the above equation.

In this way, it is advantageously possible to work in vacuum and directly connected to the accelerating structure so that the measuring device is not damaged by the beam to be measured; moreover, thanks to the non-metallic walls, the Bremsstrahlung X-rays are eliminated, thus improving the signal.

According to the technical standard EN 60601-2-1, for current variations from 120 to 60 mA, typical for the above-mentioned "Flash" effect, there is an energy increase of more than 2 MeV.

This patent provides the possibility to implement such control, significantly increasing the intrinsic safety of a radiotherapy treatment.

Starting from the demonstration of the fact that the energy gain of an electron inside a radiofrequency cavity of length L is given by $$\Delta W = \int_{-L/2}^{L/2} qE_z(r=0, z, t=z/v)dz = \int_{-L/2}^{L/2} q\hat{E}_z(z)\cos(\omega t + \varphi)dz$$

where q is the electron charge and Ez is the longitudinal component of the electric field E, equal to $$E_z(r=0,z,t)=\hat{E}_z(z)\cos(\omega t+\varphi),$$

it can be shown that, in general, $$\Delta W=qE_0 LT \cos(\varphi)$$

where $$E_0 = \frac{1}{L} \int_{-L/2}^{L/2} \hat{E}_z(z)dz; \quad T = \int_{-L/2}^{L/2} \hat{E}_z(z)\cos(\omega t(z))dz \Big/ \int_{-L/2}^{L/2} \hat{E}_z(z)dz \quad (3)$$

e0 is the mean of the longitudinal electric field and T is the so-called transit time.

In general, after the LINAC accelerator has been suitably tuned, the energy gain of an electron can be expressed as $$\Delta W_{TOT} = N_{ACC} \cdot \Delta W$$

where NACC is the number of accelerating cavities (this is valid whatever the way LINAC operates; in particular, if LINAC operates in mode $n\pi/2$ and not in mode $\pi$ the number of accelerating cavities will be equal to NACC=(NTOT+½).

It is therefore possible to determine the mean energy of the electron beam once the field E0 is known, that is to say, the mean of the electric field within a single accelerating cavity. The measurement of the electric field in a cavity is carried out through the measurement of the flow of the magnetic field through said pick-up or coil 12, placed near the wall of an accelerating cavity.

Since the ratio between B and E is fixed by the geometry of the cavity, the measured signal is proportional to the electric field Ez and, therefore, to the energy of the beam accelerated by the LINAC.

The coil 12 must be placed inside an accelerating cavity, belonging to the accelerating guide 11 so that the signal collected is sufficiently attenuated to be integrated by means of an RF diode.

Typically, the intensity of the electric field in axis in a LINAC is in the order of 10-20 MV/m.

Said coil 12 must be placed in a position away from the axis of the beam so as not to interact with the electron beam and collect a not excessively high signal; an overall attenuation of between 65 and 70 dB is generally required.

The axial accelerating electric field (along the acceleration axis of the particles, in cylindrical coordinates z axis), which transfers kinetic energy to the particles present in the accelerating cavities 10, collaterally induces the presence of an azimuth magnetic field.

The coil 12 is placed orthogonally to the azimuth direction, therefore orthogonal to the magnetic field, that is, with the surface enclosed by it arranged radially to the accelerating cavity of the above-mentioned accelerating guide 11 (surface enclosed by the coil parallel to the radial direction, in cylindrical coordinates r axis).

This coil collects a signal v(t) and transmits it to an RF diode, which temporally integrates the signal making it a low frequency signal which can be used by an electronic comparator. In this way it is possible to monitor in real time and in a non-destructive manner the actual kinetic energy of the electron beam.

It should be noted that the inductive pick-up 12 also measures the variation of the flow of magnetic field generated by the beam itself. The intensity of the beam current, as stated above, is measured by a special device and can therefore be subtracted from the signal in question, which is thus purely proportional to the energy of the beam.

Operationally, during the test phase of the medical accelerator, a simultaneous measurement of the signal v(t) measured and of the beam energy (using the water phantom method), as specified by international protocols, establishes, energy by energy, the range of values within which the signal v(t) can vary with an energy variation, as specified by EN 60601-2-1 (or in any narrower range).

In this specific case, unlike traditional technologies, precisely because of the high currents involved in generating the "Flash" effect, the energy measurement cannot be separated from current measurement, making a real-time control even more stringent than in the conventional case.

In addition, the FLASH system can operate with different optical beam systems, either with a standard collimating system, that is, fixed fields, or in pencil-beam mode.

The fixed field collimation mode can be obtained through a purely passive system, that is, with the use of a properly sized scattering filter, with the advantage of being able to implement a simple and economic solution, limiting the diffused radiation produced by the scattering filter and allowing a simple and safe installation even in unshielded operating theatres.

Figure 6:
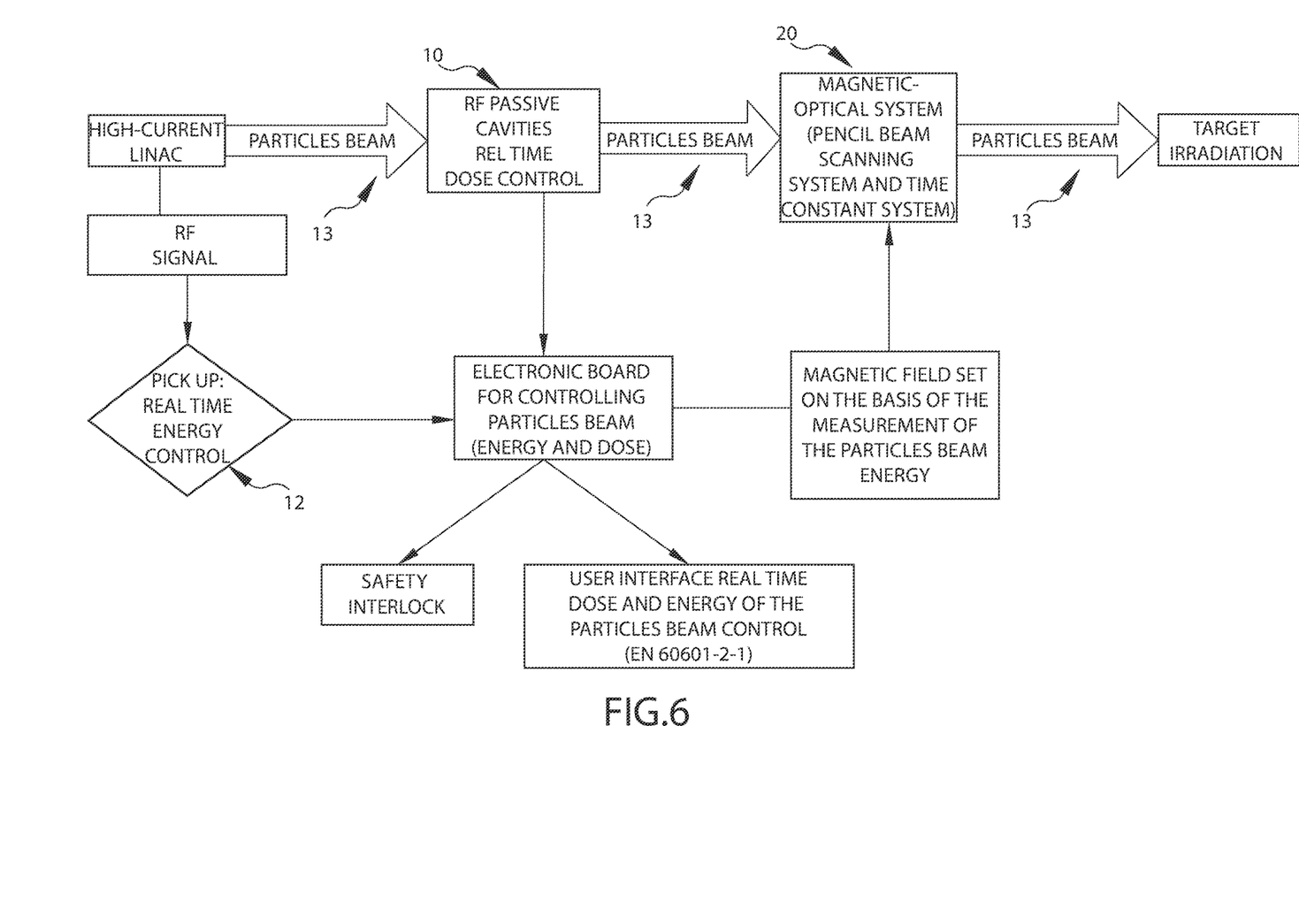
FIG. 6 represents a block diagram of the operation of a "Flash" system according to the invention.

It is also possible to use an active system, that is, for example, a set (two or three) of defocusing electromagnetic quadrupoles, as shown in FIG. 6, with the advantage of being able to use the totality of the accelerated electrons without dispersing them due to the interaction with the scattering filter and without creating Bremsstrahlung X-rays, as happens for the previous solution.

The dose rate deposited in a volume V is, in a first approximation, proportional to the IBEAM beam current which strikes it, divided by the area S:

$$\left(\frac{dD}{dt}\right)_V \approx \frac{I_{BEAM}}{S}$$

The use of an active quadrupole system makes it possible to obtain very high rates on small surfaces, and to make the dose rate inversely proportional to the surface to be treated; for example, given a dose rate of 500 Gy/s in a 10×10 cm field, the corresponding rate with an 8×8 cm field is higher than 1500 Gy/s and equal to approximately 4000 Gy/s for a 5×5 cm field.

Summing up (FIG. 6), positioned at the exit of the particle accelerator and connected to it there are passive cavities, see figure below, operating in vacuum, such as to measure, in a non-destructive manner, the current of a particle beam.

The passive cavities 10 are designed for measuring the absorbed dose of ionizing radiation.

Inside each cavity there is a pickup or coil 12B.

The dose data from said passive cavities 10 and therefore from the relative pick-up 12B_and the energy data coming from said pick-up or coil 12 are compared and controlled on an electronic board that acts as a safety switch, by the user, for their monitoring, according to the technical standard EN 60601-2-1; this is of significant importance for the high currents in play which there are with the above-mentioned "Flash" effect.

On the basis of this control the magnetic field is set and the geometry of the radiation beam reaching the target is determined through the optical system (a quadrupole is used, for example), positioned downstream of the system.

From the above description of the device for the radiotherapy treatment of cancer patients, according to the invention and according to the examples illustrated in detail in the accompanying drawings, the advantages obtained are clear, including:
- system response independent of ambient conditions (temperature, pressure and humidity);
- possibility to work in a wider signal range than standard techniques;
- implementation in any radio frequency accelerating structure;
- significant increase in the intrinsic safety of a radiotherapy treatment;
- possibility of working in a vacuum;
- troubleshooting of problems caused by damage to the measuring device (monitor chamber electrodes) by the beam to be measured;
- elimination of the Bremsstrahlung X-rays;
- linearity of the response with respect to the current, at a given fixed energy;
- compliance with the requirements of technical standard EN 60601-2-1;
- limited production cost, as compared to traditional solutions, in relation to the benefits achieved.

Lastly, all the details may be replaced by other technically equivalent elements; in particular, the invention thus conceived and illustrated is susceptible to numerous modifications and variations, all falling within the scope of the inventive concept of the attached claims.

What is claimed is:

1. A device for radiotherapy treatment with high dose rate of ionizing radiation for cancer patients, comprising:
   at least one accelerating guide (11) of a radiofrequency accelerator of a charged particles beam, in which said accelerating guide (11) comprises an accelerating cavity, said particles being adapted to generate a magnetic field perpendicular to the axis of a current beam (13) of said charged particles; and
   at least two resonant cavities (10); and
   an optical system (20) of the beam;
   wherein said at least two resonant cavities (10) being located upstream and facing said optical system (20), positioned perpendicularly to said magnetic fields and being tuned to a same resonance frequency which is equal to the working mode frequency of said accelerating guide (11);
   wherein said at least two resonant cavities (10) comprising each respectively at least one second pick-up (12B) consisting of a coil;
   wherein said at least two resonant cavities (10) and said respective at least one second pick-up (12B) are able to measure said current (13) which is proportional to the dose of a beam current absorbed by a target, said at least two resonant cavities (10) being made in order to measure independently said dose of beam current absorbed by the target;
   wherein said device further comprising:
   at least a first pick-up (12) consisting of a coil, which is comprised in said accelerating guide (11) and placed inside said accelerating cavity, in which said first pick-up (12) is positioned orthogonally to said axis of the current beam (13) and is able to measure in a non-destructive way a kinetic Energy of said charged particles beam and the flow variation of said magnetic field.

2. The device according to claim 1, further comprising an electronic control boards of the beam, which communicates with an user interface, is placed between said at least two resonant cavities (10) and said first pick-up (12).

3. The device according to claim 1, wherein said optical system (20) of the beam comprises at least one defocusing electromagnetic quadrupole.

4. The device according to claim 1, wherein each of the at least two resonant cavities (10) is made of a non-metallic material suitable for vacuum, for example KOVAR or PYREX glass.

5. The device according to claim 1, wherein each of the at least two resonant cavities (10) has the inner walls covered with a thin layer of metallic material or non metallic material, for example respectively copper or ceramic.

6. The device according to claim 1, wherein:
   A. said at least two resonant cavities (10) located at the exit of said accelerator, measure the absorbed current dose of said charged particles beam taken from said second pick-up (12B);
   B. said first pick-up (12), placed inside said accelerating cavity of said accelerating guide (11), measures in real time the energy of the charged particle beam;
   C. the values of said absorbed dose and of said energy of the charged particle beam are compared and controlled by means of said electronic control boards;
   D. said electronic control boards is controlled by a user for monitoring the values of said absorbed dose and said energy of the charged particle beam;
   E. on the basis of the control of the values of said absorbed dose and of said energy of the charged particle beam, said magnetic field and said optical system (20) are set so as to determine the geometry of said charged particle beam.

* * * * *